United States Patent
Kato et al.

(10) Patent No.: US 10,376,136 B2
(45) Date of Patent: Aug. 13, 2019

(54) CAMERA HEAD FOR ENDOSCOPE AND ENDOSCOPE APPARATUS HAVING THE SAME

(71) Applicant: OLYMPUS CORPORATION, Hachioji-shi, Tokyo (JP)

(72) Inventors: Takayuki Kato, Hachioji (JP); Makoto Tomioka, Hachioji (JP); Takahiro Inoue, Hachioji (JP); Kazuo Morita, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/690,056

(22) Filed: Aug. 29, 2017

(65) Prior Publication Data

US 2017/0354321 A1  Dec. 14, 2017

Related U.S. Application Data (63) Continuation of application No. PCT/JP2016/069627, filed on Jul. 1, 2016.

(30) Foreign Application Priority Data

Jul. 30, 2015 (JP) ................................. 2015-151136

(51) Int. Cl.
*A61B 1/00* (2006.01)
*A61B 1/04* (2006.01)
(Continued)

(52) U.S. Cl.
CPC .......... *A61B 1/051* (2013.01); *A61B 1/00096* (2013.01); *A61B 1/00186* (2013.01);
(Continued)

(58) Field of Classification Search
CPC . A61B 1/051; A61B 1/00096; A61B 1/00165; A61B 1/00186; A61B 1/00188;
(Continued)

(56) References Cited

U.S. PATENT DOCUMENTS

| 5,701,903 A | 12/1997 | Sano et al. |
| 8,827,896 B2 | 9/2014 | Tsuruta et al. |

(Continued)

FOREIGN PATENT DOCUMENTS

| JP | 08000557 A | 1/1996 |
| JP | 2005046634 A | 2/2005 |

(Continued)

OTHER PUBLICATIONS

International Preliminary Report on Patentability (IPRP) dated Feb. 8, 2018 issued in counterpart International Application No. PCT/JP2016/069627.

(Continued)

*Primary Examiner* — Timothy J Neal
*Assistant Examiner* — William B Chou
(74) *Attorney, Agent, or Firm* — Holtz, Holtz & Volek PC (57) ABSTRACT

There is provided a camera head for endoscope which enables to achieve a favorable fluorescent image in any wavelength band when the observation is switched over from a normal white-light image observation to an observation of fluorescent images of different wavelength bands. The camera head for endoscope includes a camera-head optical system which includes a spectral prism having a dichroic film which splits light from the endoscope into white light and fluorescent light, and a first image pickup element and a second image pickup element which are disposed in respective optical paths split into two by the spectral prism, and the first image pickup element is for the white-light image observation in which a white-light image is captured, and the second image pickup element is for a fluorescent-image observation in which two fluorescent images of different wavelengths are captured, and the first image pickup element is disposed at a position at which an image is formed in an optical path for the white-light image (Continued)

observation, and the second image pickup element is disposed at a position between two positions at which the two fluorescent images are formed in an optical path for the fluorescent-mage observation, and the camera head for endoscope satisfies the following conditional expression (1).

$$d \leq 9 \times P \times Fno \quad (1)$$

3 Claims, 7 Drawing Sheets (51) Int. Cl.
  *A61B 1/05*    (2006.01)
  *A61B 1/045*    (2006.01)
  *A61B 1/055*    (2006.01)

(52) U.S. Cl.
  CPC .............. *A61B 1/043* (2013.01); *A61B 1/055* (2013.01); *A61B 1/00165* (2013.01); *A61B 1/00188* (2013.01); *A61B 1/042* (2013.01); *A61B 1/045* (2013.01)

(58) Field of Classification Search
  CPC ......... A61B 1/042; A61B 1/043; A61B 1/045; A61B 1/05; A61B 1/055; A61B 1/0638
  USPC ........ 600/109, 111, 112, 113, 117, 118, 128, 600/129, 160, 166
  See application file for complete search history.

(56) References Cited

U.S. PATENT DOCUMENTS

| | | |
|---|---|---|
| 2002/0035330 A1 | 3/2002 | Cline et al. |
| 2005/0065406 A1 | 3/2005 | Cline et al. |
| 2005/0154319 A1* | 7/2005 | Cline ................. A61B 1/00009 600/478 |
| 2007/0041720 A1 | 2/2007 | Iketani |
| 2007/0046778 A1* | 3/2007 | Ishihara ............. A61B 1/00009 348/68 |
| 2008/0228037 A1 | 9/2008 | Cline et al. |
| 2009/0236541 A1 | 9/2009 | Lomnes et al. |
| 2009/0268010 A1* | 10/2009 | Zhao ................... A61B 1/00009 348/45 |
| 2009/0310345 A1* | 12/2009 | Holder ...................... F21K 9/68 362/231 |
| 2010/0198010 A1 | 8/2010 | Cline et al. |
| 2010/0210904 A1 | 8/2010 | Cline et al. |
| 2011/0285995 A1* | 11/2011 | Tkaczyk ................... G01J 3/02 356/326 |
| 2013/0235174 A1* | 9/2013 | Namii ..................... G03B 11/00 348/65 |
| 2014/0350395 A1* | 11/2014 | Shachaf ................ G06T 7/0012 29/401.1 |
| 2015/0018690 A1* | 1/2015 | Kang ...................... A61B 5/418 600/473 |
| 2015/0230698 A1 | 8/2015 | Cline et al. |
| 2017/0020377 A1* | 1/2017 | Takeuchi ........... A61B 1/00009 |

FOREIGN PATENT DOCUMENTS

| | | |
|---|---|---|
| JP | 2007050106 A | 3/2007 |
| JP | 2007097652 A | 4/2007 |
| JP | 2013172903 A | 9/2013 |
| WO | 2013121610 A1 | 8/2013 |

OTHER PUBLICATIONS

International Search Report (ISR) and Written Opinion dated Sep. 13, 2016 issued in International Application No. PCT/JP2016/069627.

* cited by examiner

FIG.7 and an optical-path length up to the second image pickup element for the fluorescent-image observation, P denotes a pitch between pixels of the first image pickup element and the second image pickup element, and Fno denotes an F-number for the camera-head optical system.

Moreover, the endoscope apparatus according to the present invention is characterized by including an endoscope and the camera head for endoscope described above, which is to be connected to the endoscope.

DETAILED DESCRIPTION OF THE INVENTION

Examples of a camera head for endoscope and an endoscope apparatus having the same according to the present invention will be described below in detail by referring to the accompanying diagrams. However, the present invention is not restricted to the examples describe below.

Figure 1A:
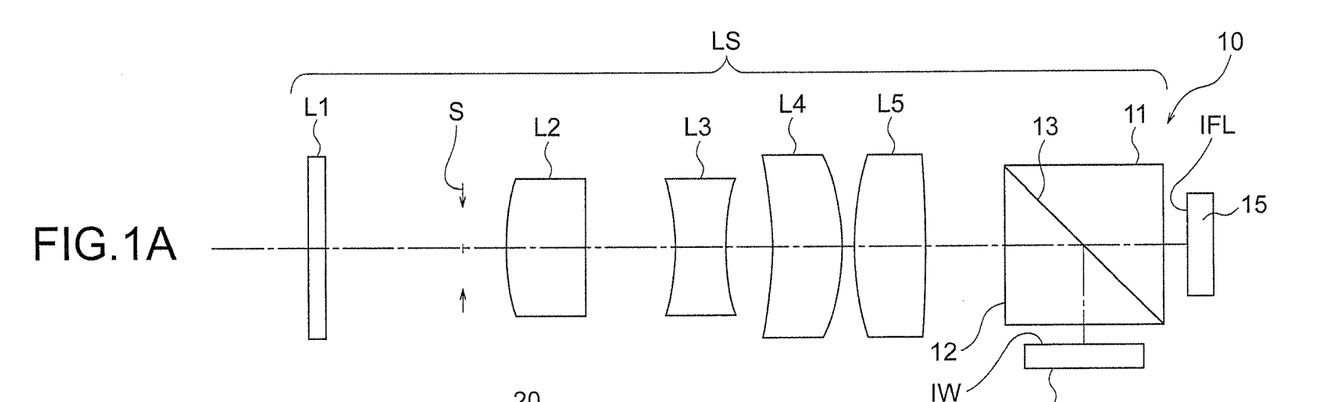
FIG. 1A is a diagram showing a lens cross-sectional view showing an arrangement of a camera head for endoscope according to an embodiment.
Figure 1B:
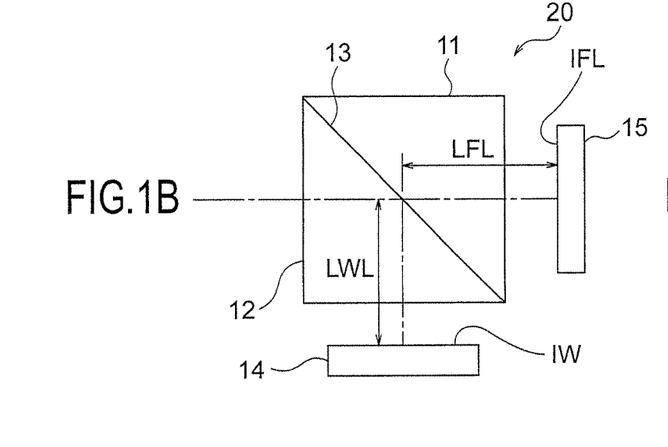
FIG. 1B is a diagram showing an arrangement near a spectral prism of the camera head for endoscope according to the embodiment.
Figure 1C:
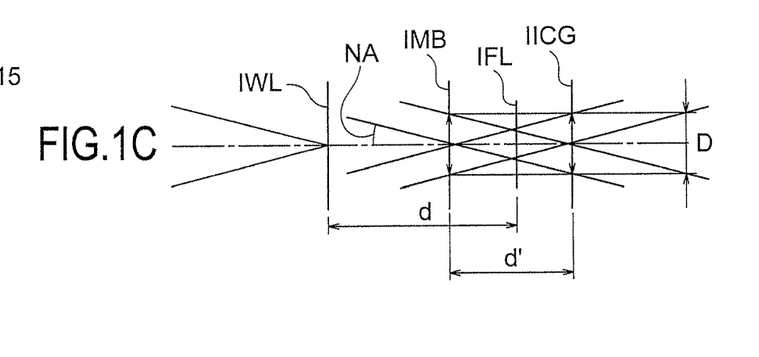
FIG. 1C is a diagram showing image plane of white-light image and image planes of fluorescent images of two different wavelength bands.

FIG. 1A is a lens cross-sectional view showing an arrangement of a camera head for endoscope according to an embodiment, FIG. 1B is a diagram showing an arrangement near a spectral prism of the camera head for endoscope according to the embodiment, and FIG. 1C is a diagram showing image plane of white-light image and image planes of fluorescent images of two different wavelength bands.

In the present embodiment, it is possible to carry out an observation of a white-light image and an observation of fluorescent images of two different wavelength bands. The two fluorescent images of two different wavelength bands are an MB fluorescent image and an ICG fluorescent image, for example.

The camera head for endoscope is to be used by connecting to an endoscope (not shown in the diagram). As shown in FIG. 1A, the camera head for endoscope includes a camera-head optical system. LS which includes a spectral prism 10 having a dichroic film 13 which splits light from the endoscope into white light and fluorescent light, and a first image pickup element 14 and a second image pickup element 15 which are disposed in respective optical paths

CAMERA HEAD FOR ENDOSCOPE AND ENDOSCOPE APPARATUS HAVING THE SAME

CROSS-REFERENCE TO RELATED APPLICATION

The present application is a continuation application of PCT/JP2016/069627 filed on Jul. 1, 2016 which is based upon and claims the benefit of priority from Japanese Patent Application No. 2015-151136 filed on Jul. 30, 2015; the entire contents of which are incorporated herein by reference.

BACKGROUND OF THE INVENTION

Field of the Invention

The present invention relates to a camera head for endoscope and an endoscope apparatus having the same.

Description of the Related Art

An electronic endoscope apparatus can be let to have an arrangement to observe a lesion part of a living tissue, and to display an auto-fluorescent observation image. With this arrangement, an image by white light is to be observed at the time of normal observation. At the time of observing a fluorescent image, an image of a fluorescent band is to be observed. An endoscope apparatus for observing a fluorescent image is proposed in Japanese Patent Application Laid-open Publication No. 2005-46634, Japanese Patent Application Laid-open Publication No. 2007-50106 and Japanese Patent Application Laid-open Publication No. Hei 8-557.

SUMMARY OF THE INVENTION

The camera head for endoscope according to the present invention, which is to be used by connecting to an endoscope, includes, a camera-head optical system which includes a spectral prism having a dichroic film which splits light from the endoscope into white light and fluorescent light, and a first image pickup element and a second image pickup element which are disposed in respective optical paths split into two by the spectral prism, wherein the first image pickup element is for a white-light image observation in which a white-light image is captured, and the second image pickup element is for a fluorescent-image observation in which two fluorescent images of different wavelengths are captured, and the first image pickup element is disposed at a position at which an image is formed in an optical path for the white-light image observation, and the second image pickup element is disposed at a position between two positions at which the two fluorescent images are formed in an optical path for the fluorescent-image observation, and the camera head for endoscope satisfies the following conditional expression (1).

$$d \leq 9 \times P \times Fno \quad (1)$$

where, d denotes a difference between an optical-path length up to the first image pickup element for the white-light image observation split into two by the spectral prism 10. The first image pickup element 14 is for a white-light image observation in which a white-light image is captured, and the second image pickup element 15 is for a fluorescent-image observation in which two fluorescent images namely, an MB fluorescent image and an ICG fluorescent image, of different wavelength are captured. The first image pickup element 14 is disposed at a position (white-light image plane IWL) at which an image is formed in an optical path for the white-light image observation, and the second image pickup element 15 is disposed at a position (fluorescent best-focused image plane IFL) between two positions (MB fluorescent image plane IMB and ICG fluorescent image plane IICG) at which the two fluorescent images namely, the MB fluorescent image and the ICG fluorescent image are formed in an optical path for the fluorescent-image observation, and the camera head for endoscope satisfies the following conditional expression (1).

$$d \leq 9 \times P \times Fno \quad (1)$$

where, d denotes a difference between an optical-path length LWL up to the first image pickup element 14 for the white-light image observation and an optical-path length 15 up to the second image pickup element 15 for the fluorescent-image observation, P denotes a pitch between pixels of the first image pickup element 14 and the second image pickup element 15, and Fno denotes an F-number for the camera-head optical system LS.

When the camera head for endoscope does not satisfy conditional expression (1), it is not possible to capture the two fluorescent images namely, the MB fluorescent image and the ICG fluorescent image favorably.

As shown in FIG. 1B, the spectral prism 10 has the dichroic film 13 which splits the light from endoscope into the white light and the fluorescent light. The first optical element 14 and the second optical element 15 are disposed on respective optical paths split into two by the spectral prism 10. The first image pickup element 14 is for the white-light image observation in which the white-light image is observed. The second image pickup element 15 is for the fluorescent-image observation in which the MB fluorescent image and the ICG fluorescent image which are two fluorescent images of different wavelengths are observed.

FIG. 1C is a diagram in which, a white-light image plane IWL which is a position of the white-light image and an MB fluorescent image plane IMB and an ICG fluorescent image plane IICG which are two fluorescent images, are shown by extending an optical axis linearly. The first image pickup element 14 is disposed at a position (white-light image plane IWL) at which an image is formed in an optical path for the white-light image observation. The second image pickup element 15 is disposed at a position (fluorescent best focused image plane IFL) between the two positions (MB fluorescent image plane IMB and the ICG fluorescent image plane IICG) at which the MB fluorescent image and the ICG fluorescent image which are two fluorescent images, are formed in an optical path for the fluorescent image observation.

Figure 2:
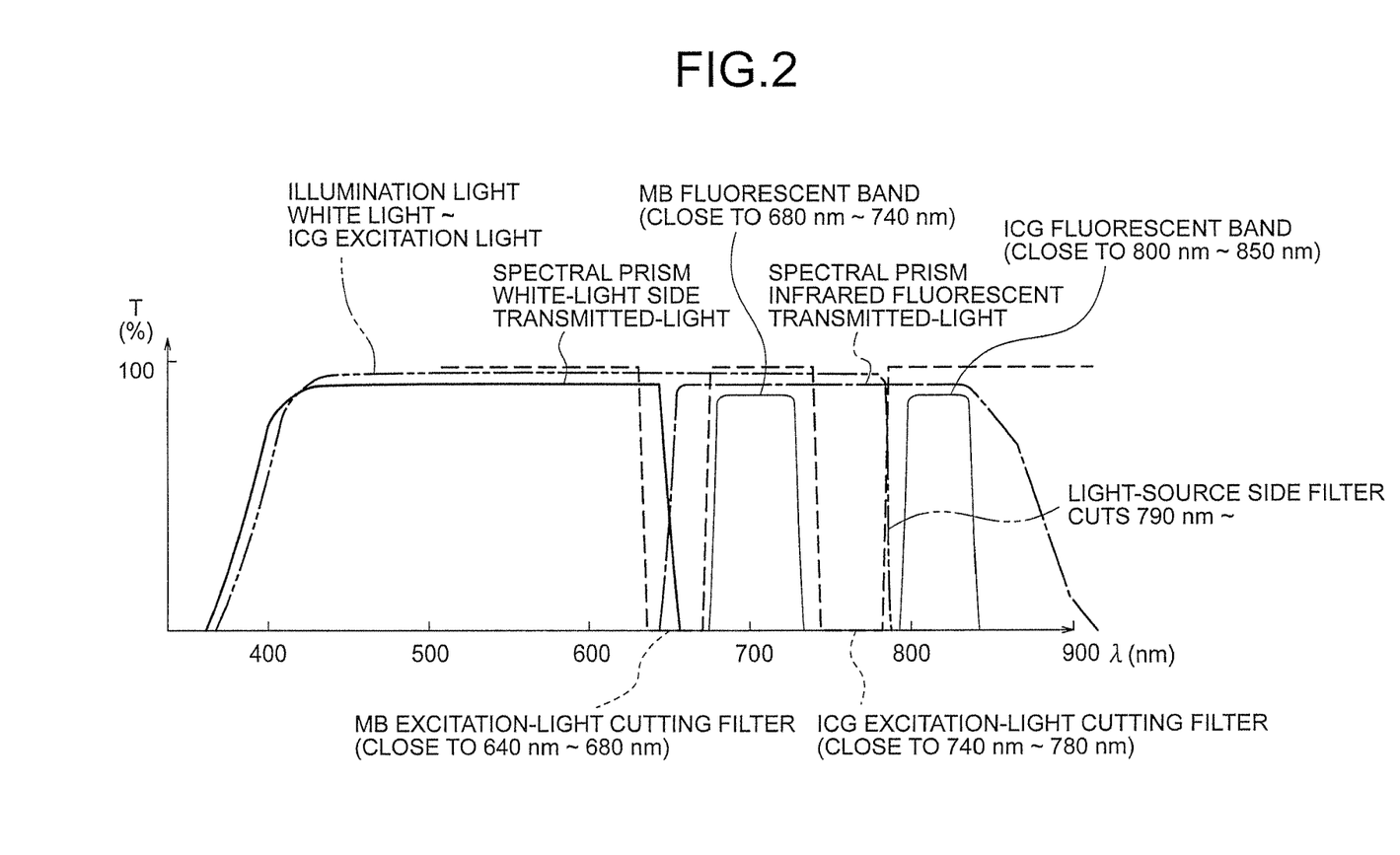
FIG. 2 is a diagram showing a spectral distribution of white light and fluorescent light of two different wavelengths.

Moreover, FIG. 2 is a diagram showing a wavelength band of the white light in the present embodiment, wavelength bands of fluorescent images for two different wavelength bands, a spectral distribution of a wavelength of excitation light, and a filter transmittance. A horizontal axis indicates wavelength (unit: nm), and a vertical axis indicates transmittance (unit: %).

As shown in FIG. 2, the MB fluorescent image has a wavelength band close to 680 nm~740 nm. The ICG fluorescent image has a wavelength band close to 800 nm~850 nm.

A plane parallel plate L1 is an MB excitation-light cutting filter (close to 640 nm~680 nm) and an ICG excitation-light cutting filter (close to 740 um~780 nm).

Next, conditional expression (1) will be described below.

$$d \leq 9 \times P \times Fno \quad (1)$$

where, d denotes a difference (LFL-LWL) between an optical-path length LWL up to the first image pickup element 14 for the white-light image observation and an optical path length LFL up to the second image pickup element 15 for the fluorescent-image observation, P denotes a pitch between pixels of the first image pickup element 14 and the second image pickup element 15, and Fno denotes an F-number for the camera-head optical system LS.

The parameter P will be described further by referring to FIG. 10, and FIG. 3A, FIG. 3B, and FIG. 3C. In FIG. 10, a ratio of the distance between the white-light image plane IWL and the MB fluorescent image plane IMB and the distance between the MB fluorescent image plane IMB and the ICG fluorescent image plane IICG is substantially 1 to 1. Furthermore, the second image pickup element 15 for the fluorescent image is disposed at a position substantially half-way of the MB fluorescent image plane IMB and the ICG fluorescent image plane IICG.

Therefore, a distance d' between the MB fluorescent image plane IMB and the ICG fluorescent image plane IICG is indicated by the following expression (2).

$$d' \approx (2/3) \times d \quad (2)$$

Moreover, NA is indicated by the following expression (3).

$$NA = 1/(2 \times Fno) \quad (3)$$

Here, when the white-light image is at the best-focused position on the first image pickup element 14, the maximum light-beam diameter, which the MB fluorescent image and the ICG fluorescent image can have on the second image pickup element 15, is let to be D.

Expression (3) can be rewritten as follows.

$$D = 2 \times NA \times d'$$

$$D = 2 \times 1/(2 \times Fno) \times (2/3) \times d$$

$$d = (3/2) \times D \times Fno \quad (4)$$

Figure 3A:
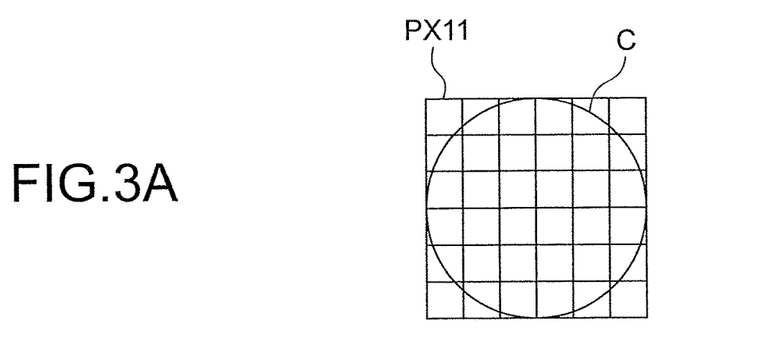
FIG. 3A is a diagram showing a relationship of a circle of least confusion and pixels.

For both the MB fluorescent image and the ICG fluorescent image to be in a depth of field, it is preferable that D becomes smaller than a diameter (=6×P) of a circle of confusion as shown in FIG. 3A.

$$D \leq 6 \times P \quad (5)$$

When expression (5) is substituted in expression (4), the following conditional expression (1) can be achieved.

$$d \leq 9 \times P \times Fno \quad (1)$$

It is desirable to satisfy the following conditional expression (1') instead of conditional expression (1).

$$d \leq 6 \times P \times Fno \quad (1')$$

Furthermore, it is more desirable to satisfy the following conditional expression (1″) instead of conditional expression (1).

$$d \leq 3 \times P \times Fno \quad (1″)$$

Figure 3B:
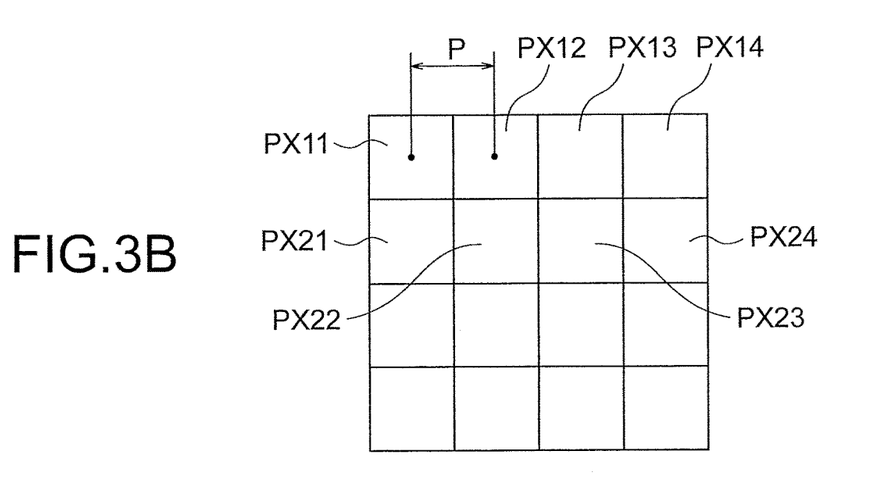
FIG. 3B is a diagram showing a pitch of pixels.

Next, the pitch P of pixels will be described below. FIG. 3B shows schematically some pixels PX11 to PX24 of the first image pickup element 14 and the second image pickup element 15. Here, the pitch P of pixels is a distance between centers of two adjacent pixels such as PX11 and PX12.

Moreover, as a method for improving a sensitivity of detection of an image pickup element, binning has been known. In the binning, a plurality of pixels is combined artificially and treated as one pixel, and the sensitivity of detection is improved by making large virtually, the number of image pickup elements included in this new pixel.

Figure 3C:
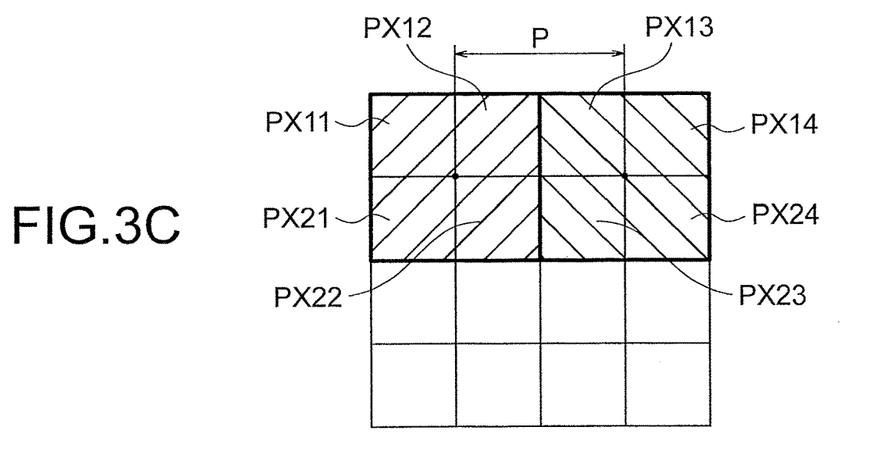
FIG. 3C is a diagram showing the pitch of pixels when binning has been carried out.

FIG. 3C shows an arrangement when 2×2, that is 4 adjacent pixels PX11, PX12, PX21, and PX 22 are treated as one pixel artificially. In a case of carrying out the binning, a distance between centers of four pixels that are combined is let to be the pitch P. The binning is not restricted to combining only 2×2 pixels, and an arbitrary number of pixels can be combined.

Example 1

Figure 4:
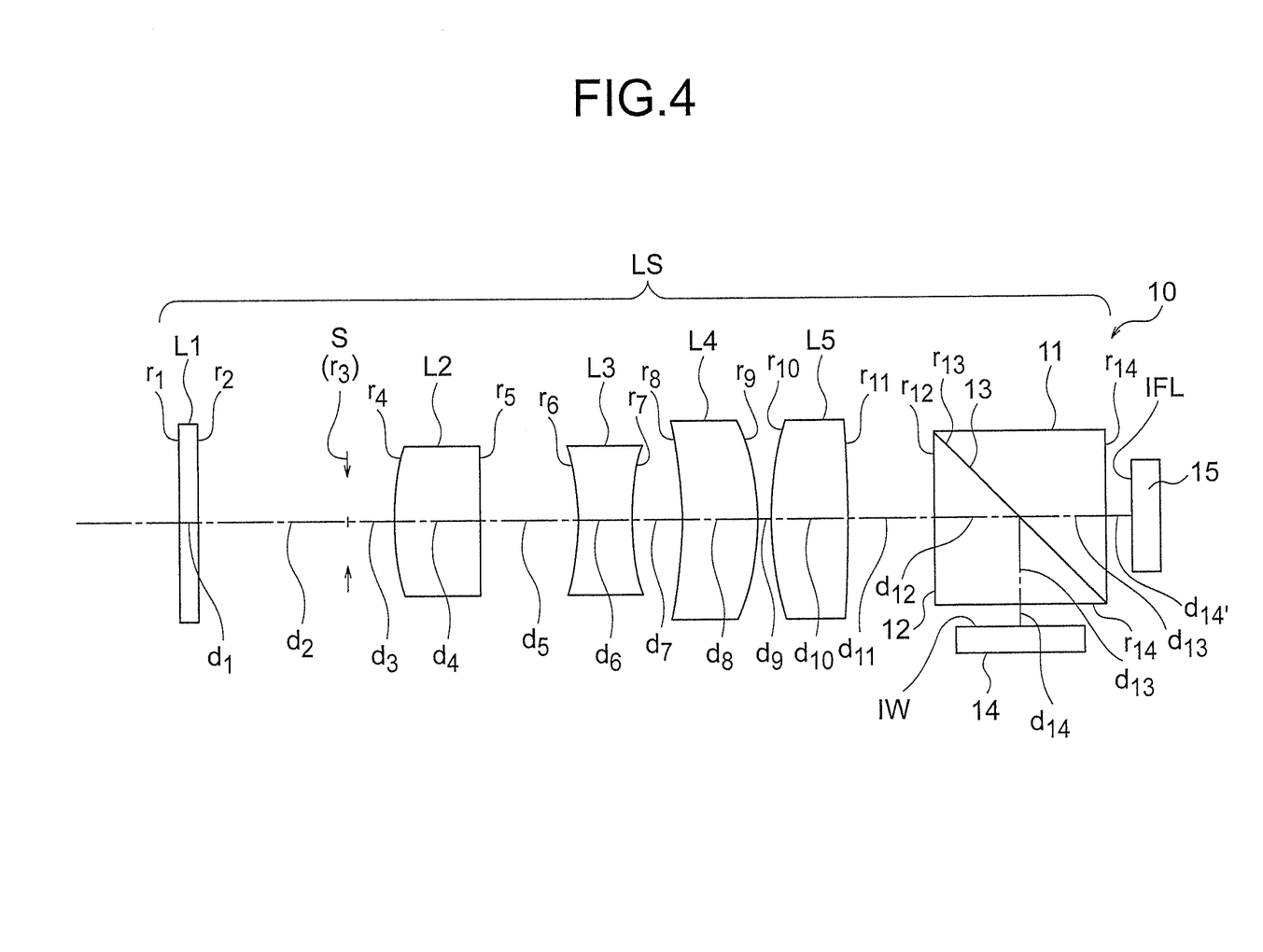
FIG. 4 is a cross-sectional view showing an optical system of a camera head for endoscope according to an example 1.

A camera head for endoscope according to an example 1 will be described below. FIG. 4 is a cross-sectional view showing an optical system of the camera head for endoscope according to the example 1.

A camera head for endoscope LS includes in order from an object side (endoscope side), a plane parallel plate L1, a planoconvex positive lens L2 having a convex surface directed toward the object side, a biconcave negative lens L3, a positive meniscus lens L4 having a convex surface directed toward an image side, a biconvex positive lens L5, and the spectral prism 10.

The spectral prism 10 is formed by cementing two right-angle prisms 11 and 12 sandwiching the dichroic film 13. The dichroic film 13 reflects white light out of light from the endoscope, and splits by allowing the MB fluorescent light and the ICG fluorescent light to be transmitted. The first image pickup element 14 is for the white-light image observation in which the white-light image is captured. The second image pickup element 15 is for the fluorescent-image observation in which, the MB fluorescent image and the ICG fluorescent image which are the two fluorescent images of different wavelengths, are captured.

Moreover, the plane parallel plate L1 is an MB excitation-light cutting filter (close to 640 nm~680 nm) and an ICG excitation-light cutting filter (740 nm~780 nm).

Example 2

Figure 5:
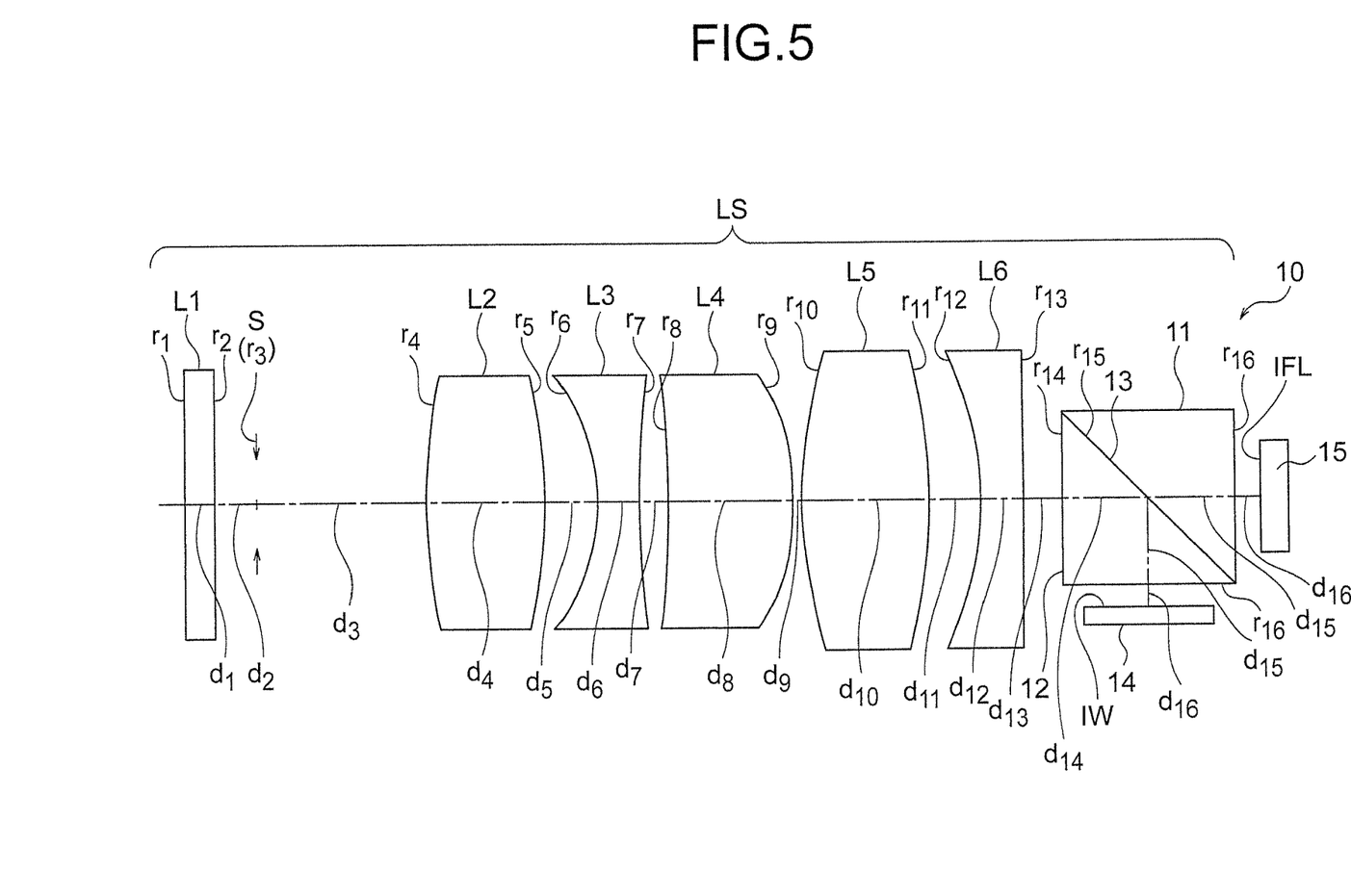
FIG. 5 is a cross-sectional view showing an optical system of a camera head for endoscope according to an example 2.

A camera head for endoscope according to an example 2 will be described below. FIG. 5 is a cross-sectional view showing an optical system of the camera head for endoscope according to the example 2.

A camera head for endoscope LS includes in order from an object side (endoscope side), a plane parallel plate L1, an aperture stop S, a biconvex positive lens L2, a biconcave negative lens L3, a positive meniscus lens L4 having a convex surface directed toward an image side, a biconvex positive lens L5, a planoconcave negative lens L6 having a concave surface directed toward the object side, and the spectral prism 10.

The spectral prism 10 is formed by cementing two right-angle prisms 11 and 12 sandwiching the dichroic film 13. The dichroic film 13 reflects white light out of light from the endoscope, and splits by allowing the MB fluorescent light and the ICG fluorescent light to be transmitted. The first image pickup element 14 is for the white-light image observation in which the white-light image is captured. The second image pickup element 15 is for the fluorescent-image observation in which the MB fluorescent image and the ICG fluorescent image which are the two fluorescent images of different wavelengths are captured.

Moreover, the plane parallel plate L1 is an MB excitation-light cutting filter (close to 640 nm~680 nm) and an ICG excitation-light cutting filter (740 nm~780 nm).

Example 3

Figure 6:
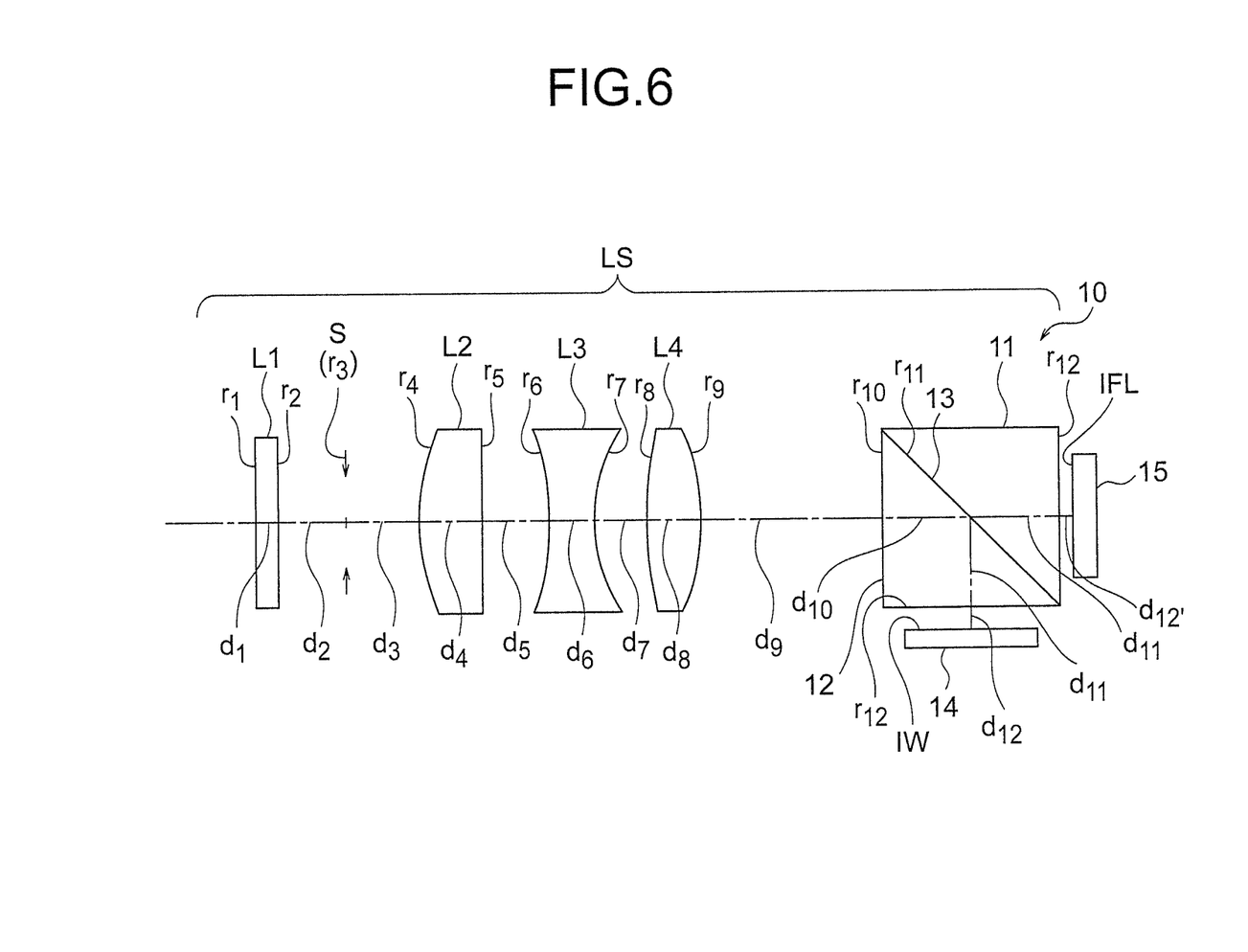
FIG. 6 is a cross-sectional view showing an optical system of a camera head for endoscope according to an example 3.

A camera head for endoscope according to an example 3 will be described below. FIG. 6 is a cross-sectional view showing an optical system of the camera head for endoscope according to the example 3.

A camera head for endoscope LS includes in order from an object side (endoscope side), a plane parallel plate L1, an aperture stop S, a planoconvex positive lens L2 having a convex surface directed toward the object side, a biconcave negative lens L3, a biconvex positive lens L4, and the spectral prism 10.

The spectral prism 10 is formed by cementing two right-angle prisms 11 and 12 sandwiching the dichroic film 13. The dichroic film 13 reflects white light out of light from the endoscope, and splits by allowing the MB fluorescent light and the ICG fluorescent light to be transmitted. The first image pickup element 14 is for the white-light image observation in which, the white-light image is captured. The second image pickup element 15 is for the fluorescent-image observation in which the MB fluorescent image and the ICG fluorescent image which are the two fluorescent images of different wavelengths are captured.

Moreover, the plane parallel plate L1 is an MB excitation-light cutting filter (close to 640 nm~680 nm) and an ICG excitation-light cutting filter (740 nm~780 nm).

Example 4

Figure 7:
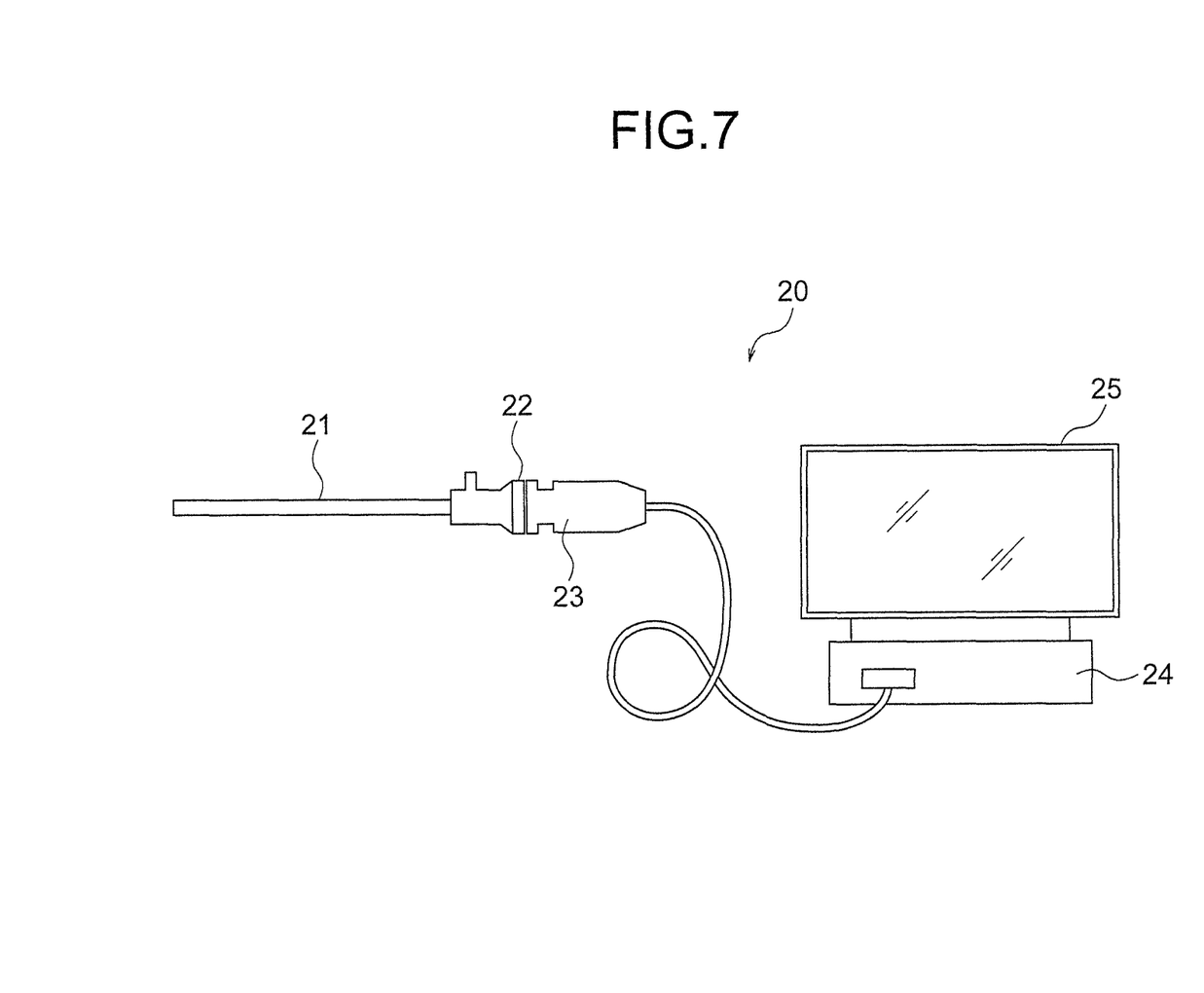
FIG. 7 is a diagram showing a schematic arrangement of an endoscope apparatus according to an example 4.

FIG. 7 shows an arrangement of an endoscope apparatus 20 according to an example 4. The endoscope apparatus 20 includes a light-source for illumination, a rigid endoscope 21, and the abovementioned camera head for endoscope 23 which is to be connected to a connecting portion 22 of the hard endoscope 21. An output signal from the camera head for endoscope 23 is input to a camera control unit 24. A white-light image, an MB fluorescent image, and an ICG fluorescent image are displayed on a monitor 25.

In the present example, for the parameter Fno, in a state of the camera head for endoscope 23 being used by connecting to the hard endoscope 21, an F-number of a combined system of the camera-head optical system. LS and an optical system in the hard endoscope 21 may be used instead of an F-number for the camera-head optical system LS.

Numerical data for each example is shown below. Regarding symbols, r denotes a radius of curvature of each lens surface, di denotes a distance between lens surfaces, ne denotes a refractive index for an e-line of each lens, vd denotes Abbe's number for each lens, and Fno denotes the F-number.

Example 1

Unit mm

Surface data

| Surface no. | r | di | ne | νd |
|---|---|---|---|---|
| 1 | ∞ | 0.7 | 1.77066 | 71.79 |
| 2 | ∞ | 6.1 | | |
| 3(Stop Φ3.6 mm) | ∞ | 1.9 | | |
| 4 | 10.484 | 3.5 | 1.79196 | 47.37 |
| 5 | ∞ | 4 | | |
| 6 | −11.061 | 2.2 | 1.85504 | 23.78 |
| 7 | 11.061 | 2 | | |
| 8 | −22.182 | 3.1 | 1.73234 | 54.68 |
| 9 | −10.691 | 0.54 | | |
| 10 | 13.408 | 3.1 | 1.79196 | 47.37 |
| 11 | −60.966 | 3.5073 | | |
| 12 | ∞ | 3.5 | 1.51825 | 64.14 |
| 13 | ∞ | 3.5 | 1.51825 | 64.14 |
| 14 | ∞ | 1 | | |
| Image plane IWL | ∞ | 0 | | |
| Image plane IFL | ∞ | 0.125 | | |

Reference wave length: e-line
Various data

| Fno | 5.127 |
|---|---|
| P | 2.8 μm |
| Object distance | 1000 mm (−1 diopter) |
| Maximum image height | 2.24 mm |

Example 2

Unit mm

Surface data

| Surface no. | r | di | ne | νd |
|---|---|---|---|---|
| 1 | ∞ | 0.8 | 1.51825 | 64.14 |
| 2 | ∞ | 1.0 | | |
| 3(Stop Φ2.8 mm) | ∞ | 4 | | |
| 4 | 13.55 | 2.8 | 1.8393 | 37.34 |
| 5 | −13.55 | 1.249 | | |
| 6 | −4.77 | 1 | 1.85538 | 23.78 |
| 7 | 24.4 | 0.668 | | |
| 8 | −30.35 | 3 | 1.80811 | 46.5 |
| 9 | −6 | 0.2 | | |
| 10 | 12 | 3 | 1.80811 | 46.5 |
| 11 | −12 | 1.178 | | |
| 12 | −7.85 | 1 | 1.81245 | 25.46 |
| 13 | ∞ | 1 | | |
| 14 | ∞ | 2 | 1.51825 | 64.14 |
| 15 | ∞ | 2 | 1.51825 | 64.14 |
| 16 | ∞ | 0.4925 | | |
| Image plane IWL | ∞ | 0 | | |
| Image plane IFL | ∞ | 0.02 | | |

Reference wave length: e-line
Various data

| Fno | 3.215 |
|---|---|
| P | 1 μm |
| Object distance | 1000 mm (−1 diopter) |
| Maximum image height | 1.2 mm |

Example 3

Unit mm

Surface data

| Surface no. | r | di | ne | νd |
|---|---|---|---|---|
| 1 | ∞ | 2 | 1.51825 | 64.14 |
| 2 | ∞ | 6 | 1 | |
| 3(Stop Φ2.8 mm) | ∞ | 6.61 | 1 | |
| 4 | 20.434 | 5.5 | 1.77621 | 49.6 |
| 5 | ∞ | 5.97 | 1 | |
| 6 | −26.052 | 4 | 1.73429 | 28.46 |
| 7 | 14.454 | 4.72 | 1 | |
| 8 | 37.901 | 4.8 | 1.75844 | 52.32 |
| 9 | −21.072 | 15.8039 | 1 | |
| 10 | ∞ | 8 | 1.51825 | 64.14 |
| 11 | ∞ | 8 | 1.51825 | 64.14 |
| 12 | ∞ | 1 | | |
| Image plane IWL | ∞ | 0 | | |
| Image plane IFL | ∞ | 0.2 | | |

Reference wave length: e-line
Various data

| Fno | 5.229 |
|---|---|
| P | 4.4 μm |
| Object distance | 1000 mm (−1 diopter) |
| Maximum image height | 5.5 mm |

Values of the conditional expressions of each of examples are shown below.

| | Example1 | Example2 | Example3 |
|---|---|---|---|
| d | 0.125 | 0.02 | 0.2 |
| 9 × P × Fno | 0.1292 | 0.0289 | 0.2071 |

In the embodiments and examples, description has been made by citing the MB fluorescent image and the ICG fluorescent image as examples of the fluorescent images of different wavelengths. However, the present invention is not restricted to this, and is also applicable to fluorescent images of other wavelengths.

Various embodiments of the present invention have been described above. However, the present invention is not restricted to these embodiments, and embodiments arranged by combining these embodiments appropriately, without departing from the scope of the present invention also fall under the category of the present invention.

As described above, the camera head for endoscope according to the present invention and the endoscope apparatus having the same are useful for the white-light image observation and for observing fluorescent images of different wavelength bands.

According to the present invention, an effect is shown that it is possible to provide a camera head for endoscope which enables to achieve a favorable fluorescent image in any wavelength band when the observation is switched over from a normal white-light image observation to an observation of fluorescent images of different wavelength bands, and an endoscope apparatus having the same.

What is claimed is:
1. A camera head connectable to an endoscope, the camera head comprising:
  a camera-head optical system which includes a spectral prism having a dichroic film, the spectral prism splitting light from the endoscope into white light and fluorescent light; and a first image pickup element and a second image pickup element which are disposed in respective optical paths split by the spectral prism, wherein:

the first image pickup element is used for a white-light image observation in which a white-light image is captured, and the second image pickup element is used for a fluorescent-image observation in which two fluorescent images of different wavelengths are captured, the first image pickup element is disposed at a position at which an image is formed in an optical path for the white-light image observation, the second image pickup element is disposed at a position between two positions at which the two fluorescent images are formed in an optical path for the fluorescent-image observation, and the camera head satisfies the following conditional expression (1)

$$d \leq 9 \times P \times Fno \qquad (1)$$

where, d is nonzero and denotes a difference between (i) an optical-path length from the dichroic film up to the first image pickup element for the white-light image observation and (ii) an optical-path length from the dichroic film up to the second image pickup element for the fluorescent-image observation, P denotes a pitch between pixels of each of the first image pickup element and the second image pickup element, and Fno denotes an F-number for the camera-head optical system.

2. The camera head according to claim 1, wherein the pitch is one of (i) a pitch between adjacent pixels of each of the first image pickup element and the second image pickup element, and (ii) a pitch between pixels when a plurality of pixels are combined to be one pixel.

3. An endoscope apparatus, comprising:

an endoscope; and a camera head connectable to the endoscope to be used with the endoscope, the camera head comprising:

a camera-head optical system which includes a spectral prism having a dichroic film, the spectral prism splitting light from the endoscope into white light and fluorescent light; and a first image pickup element and a second image pickup element which are disposed in respective optical paths split by the spectral prism, wherein:

the first image pickup element is used for a white-light image observation in which a white-light image is captured, and the second image pickup element is used for a fluorescent-image observation in which two fluorescent images of different wavelengths are captured, the first image pickup element is disposed at a position at which an image is formed in an optical path for the white-light image observation, the second image pickup element is disposed at a position between two positions at which the two fluorescent images are formed in an optical path for the fluorescent-image observation, and the camera head satisfies the following conditional expression (1)

$$d \leq 9 \times P \times Fno \qquad (1)$$

where, d is nonzero and denotes a difference between (i) an optical-path length from the dichroic film up to the first image pickup element for the white-light image observation and (ii) an optical-path length from the dichroic film up to the second image pickup element for the fluorescent-image observation, P denotes a pitch between pixels of each of the first image pickup element and the second image pickup element, and Fno denotes an F-number for the camera-head optical system.

* * * * *